United States Patent [19]
Townsend et al.

[11] Patent Number: 5,259,832
[45] Date of Patent: Nov. 9, 1993

[54] MULTIAXIS CONTROLLED MOTION KNEE BRACE WITH A FOUR BAR JOINT AND METHOD FOR PRODUCING SAME

[75] Inventors: Jeffrey H. Townsend, 7106 Crestwood St., Bakersfield, Calif. 93304; Robert J. Williams, Shoreview, Minn.

[73] Assignee: Jeffrey H. Townsend, Bakersfield, Calif.

[21] Appl. No.: 664,983

[22] Filed: Mar. 6, 1991

[51] Int. Cl.$^5$ .................................................. A61F 5/00
[52] U.S. Cl. ........................................ 602/16; 602/26
[58] Field of Search ................ 602/16, 23, 26, 27; 16/357, 358, 366, 368, 369, 371, 374

[56] References Cited

U.S. PATENT DOCUMENTS

| Re. 33,621 | 6/1991 | Lamb et al. ................ 602/16 |
| 3,823,424 | 7/1974 | May . |
| 3,826,251 | 7/1974 | Ross . |
| 4,463,751 | 8/1984 | Bledsoe ........................ 602/16 |
| 4,655,201 | 4/1987 | Pirmartgen ................... 602/16 |
| 4,699,129 | 10/1987 | Auserude et al. ............. 602/16 |
| 4,723,539 | 2/1988 | Townsend ..................... 602/16 |
| 4,886,054 | 12/1989 | Castillo et al. ............... 602/26 |
| 4,890,607 | 1/1990 | Townsend ..................... 602/16 |
| 5,022,391 | 6/1991 | Weidenburner ............... 602/16 |

FOREIGN PATENT DOCUMENTS

| 2231356 | 12/1974 | France . |
| 2600528 | 12/1987 | France . |

*Primary Examiner*—Richard J. Apley
*Assistant Examiner*—Linda C. M. Dvorak
*Attorney, Agent, or Firm*—Sixbey, Friedman, Leedom & Ferguson

[57] ABSTRACT

A knee brace has a pair of femoral and tibial links and a four bar joint mechanism by which a lateral side one of the femoral links is pivotally connected to a lateral side one of the tibial links and a four bar joint mechanism by which a medial side one of the femoral links is pivotally connected to a medial side one of the tibial links. Each of the joint mechanisms comprises an inner, padded, pivot plate and an outer pivot plate, each of end of which is pivotally connected at a single point to a respective one of the femoral and tibial links. Furthermore, the pad on the inner pivot plate of the medial side joint mechanism carries a spherically cupped femoral condyle pad by which the brace, generally, and the joint mechanism, specifically, can be properly positioned relative to the knee of the wearer. The locations of the pivot points for the pivot plates on the links are set in accordance with parameters which are designed to produce a multiaxis motion of a reference point which will constrain the tibia to slide rearwardly relative to the femur in an initial range of flexion of the knee from a straight leg position and then to rotate relative thereto along an arcuate path. Additionally, the angle between imaginary lines through the pivots of each pivot plate is caused to be greater than a predetermined minimum value which will insure that the joint mechanism has sufficient strength not to break apart in use due to loads which are imposed horizontally across the knee joint.

15 Claims, 14 Drawing Sheets

POSITION "0"

POSITION "0"

POSITION "5"

POSITION "5"

POSITION "10"

POSITION "10"

POSITION "15"

POSITION "15"

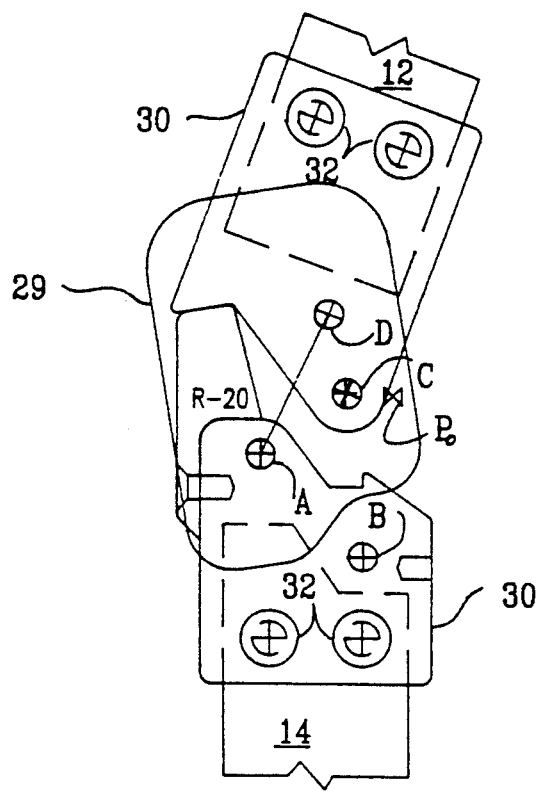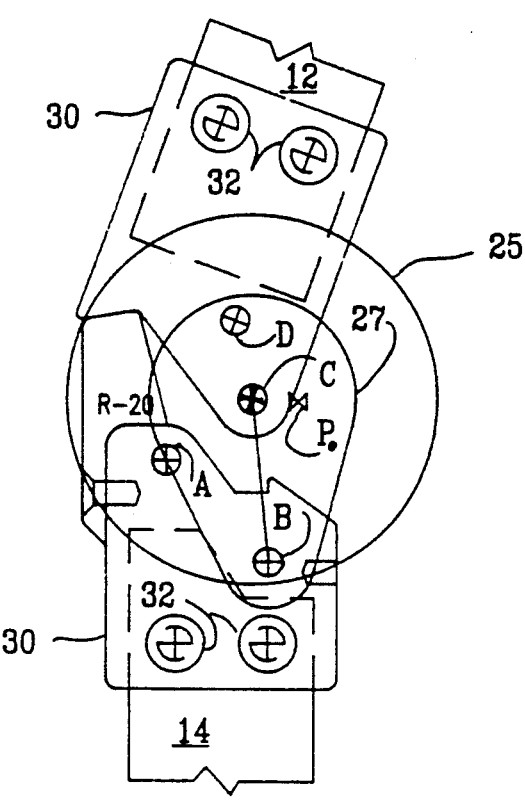

POSITION "30"

POSITION "30"

POSITION "60"  POSITION "60"

Fig. 14a
Fig. 14b
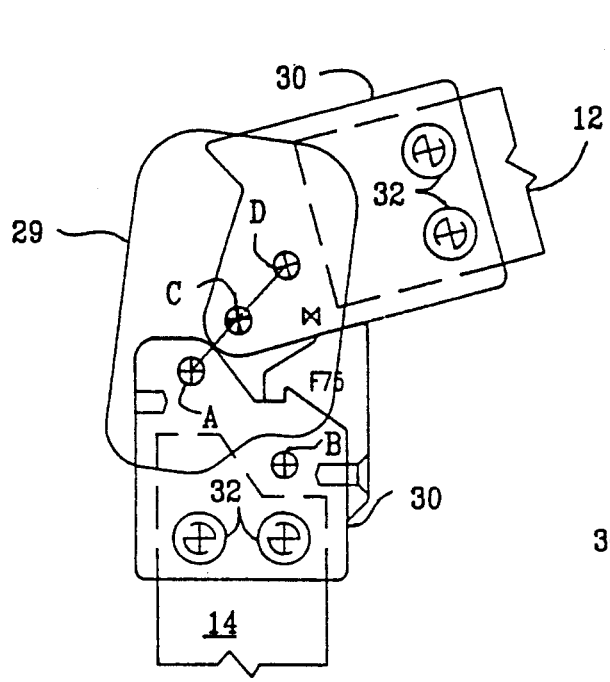
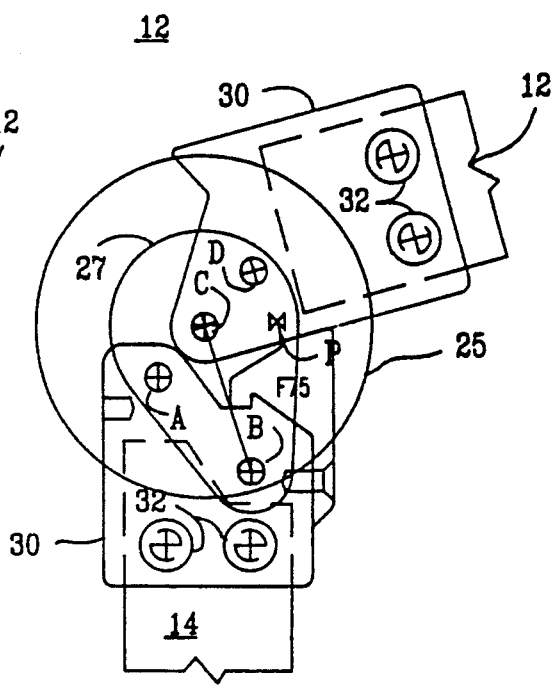
POSITION "75"
POSITION "75"

POSITION "90"

POSITION "90"

POSITION "125"

POSITION "125"

MULTIAXIS CONTROLLED MOTION KNEE BRACE WITH A FOUR BAR JOINT AND METHOD FOR PRODUCING SAME

BACKGROUND OF THE INVENTION

1. Field of the Invention

The present invention relates to orthopedic devices for the stabilization and control of a human knee joint which has been injured. More particularly, the invention relates to a knee brace which will permit the user a relatively high degree of freedom in the use of the bones while, at the same time, permitting control of the joint so as to optimize healing and stability.

2. Description of Related Art

A knee brace of the initially mentioned type is disclosed in one of the present inventor's U.S. Pat. No. 4,890,607. In this patent, a multiaxis controlled motion knee orthosis utilizes a joint mechanism (which is improved over one disclosed in U.S. Pat. No. 4,723,539 of one of the present inventors (Townsend)) having two camming slots and cam pin followers, wherein one camming slot is disposed in a transverse plane and serves to provide the anterior motion of an upper joint piece, while the second camming slot is disposed in a longitudinal orientation and to provide a long arc segment for a unicentric phase of the joint arthrokinematics. During an initial range of motion, pivoting occurs through a short arc segment about an upper cam pin within the longitudinally extending arcuate slot. After the lower cam pin follower reaches the anterior end of the transverse slot, the lower cam pin follower serves as an axis of rotation or pivot point for movement of the upper cam pin follower along the long arc segment of the longitudinal slot.

Such an arrangement provides full control of the forceful action of the joints throughout the entire range of motion while providing a joint of high strength. Furthermore, in knee braces that are custom fit to a particular user, the orthosis of this earlier patent has proved very successful and has been free of significant problems. However, certain shortcomings have been encountered with regard to use of this dual pin and cam slot joint arrangement in less expensive knee braces intended for "off-the-shelf" use. In particular, a generic "off-the-shelf" unit must be fitted by the doctor to a particular user and often involves bending of the femoral and tibial links, such as by bending the femoral links outwardly and the tibial links inwardly to fit someone with larger than average thighs and smaller than average calves.

If such "doctoring" of an "off-the-shelf" unit results in the overlapping surfaces of the joint not being exactly square, these relatively large overlapping surfaces of the links are caused to bind against each other to an extent affecting the performance of the joint. More specifically, this binding produces excessive wearing of the joint, so that the critical tolerances necessary to proper control of the knee can soon be lost. Furthermore, since, during each phase of movement, the motion of the joint is occurring about a single pivot, the full effect of the binding force is concentrated at the single pivot, and is sufficiently great to cause the binding effect to be felt by the wearer to an undesirable degree.

At the other end of the spectrum, in top of the line knee braces, especially for use by professional athletes, the weight of the knee brace is an important consideration, as is high resistance to wear. One way to reduce the weight of the joint, while increasing wear-resistance would be to form the femoral and tibial links of a "space age" lightweight fiber and resin composite material. However, such materials are expensive to machine and are very notch sensitive. Thus, a link having slots as disclosed in the above-mentioned Townsend patents would be cost-prohibitive to produce of a composite material, and would be prone to break apart due to the low notch strength of the composite material.

Thus, it would be desirable and advantageous to produce a joint which would have the benefits of the earlier Townsend designs without their shortcomings. In particular, to have a knee brace with a joint that could be used in inexpensive "off-the-shelf" orthosis without resulting in the wearer feeling a significant binding effect or the joint experiencing excessive wear due to binding. At the same time, such an improved knee brace should possess the capability to be manufactured of lightweight, wear-resistant composite materials.

Four bar linkages are also known for use in knee braces, even for producing polycentric motion. For example, U.S. No. 3,901,223, discloses a knee joint for orthopedic supports and splints using a four bar linkage in which a pair of different length, swinging links pivotally interconnect with bearing points on head portions formed on the ends of femoral (thigh) and tibial (shin) struts. These swinging links and their respective pivot points are designed so that, during flexion of the femoral link relative to the tibial link from a fully extended position of the joint, the longer, forward, link first pivots forwardly through a given angle and then its motion reverses so that the forward link adopts an identical position relative to the tibial link in the fully flexed attitude of the joint (approximately 134° degrees) as it held in the fully extended position. This movement is intended to simulate a movement of the knee in which the locus of the instantaneous centers of rotation approximates a downward and forward curving path, beginning about 3 inches up on the femur and ending at about the position of the femoral epicondyles.

In U.S. Pat. No. 4,821,707 to Audette, a mechanical articulated joint for a knee brace is shown which also uses a four bar type linkage in an attempt to produce a joint which will duplicate the complex motion of the knee; however, at best, the linkage as disclosed in this patent can only do so in a most general way do to the approach taken therein. Furthermore, the design criteria outlined in this patent require that the shape of the condyle be known (which is difficult to do in practice), require use of an arbitrarily set reference line segment and the location of the point of tangency of this arbitrary line segment and the condyle at three positions. As a result, an "off-the-shelf," generic knee brace is virtually impossible to produce in accordance with this patent's teachings, and even achieving of a custom design brace that forces the knee to follow a motion that correctly reproduces the proper complex motion of a healthy knee is problematic.

Thus, there is still a need for controlled motion multiaxis joint for a knee brace which will meet the needs for both "off-the-shelf" and custom top-end knee braces, to an even greater extent than the cam and slot knee orthosis, mentioned above, being less prone to binding problems and being able to be made of composite fiber and resin materials; yet, at the same time, still being able to constrain the tibia to slide rearwardly relative to the femur in an initial range of flexion of the knee from a straight leg position and then to rotate relative thereto along an arcuate path.

SUMMARY OF THE INVENTION

In view of the foregoing it is a primary object of the present invention to produce a knee brace having a multiaxis controlled motion knee joint which will sufficiently closely duplicate the type of complex sliding and rotating motion achieved, previously, only through cam pin and slot type joints in a four bar type joint which will be producible from composite material when its lighter weight and improved wear resistance outweigh cost considerations and can be used in generic off-the-shelf knee braces without being subject to problems of unacceptably high wear or binding.

In keeping with the above object, it is a more specific object to provide a four bar knee brace with a joint which will constrain the tibia to slide rearwardly relative to the femur in an initial range of flexion of the knee from a straight leg position and then to rotate relative thereto along an arcuate path, yet will have sufficient strength not to break apart in use.

It is yet another object of the present invention to provide a method for producing a knee brace fulfilling the preceding objects.

These and other objects and characteristics of the present invention are achieved in accordance with a preferred embodiment, wherein the knee brace has a pair of femoral and tibial links and a four bar joint mechanism by which a lateral side one of the femoral links is pivotally connected to a lateral side one of the tibial links and a four bar joint mechanism by which a medial side one of the femoral links is pivotally connected to a medial side one of the tibial links. Each of the joint mechanisms comprises an inner, padded, pivot plate and an outer pivot plate, each end of which is pivotally connected at a single point to a respective one of the femoral and tibial links. Furthermore, the pad on the inner pivot plate of the medial side joint mechanism carries a spherically cupped femoral condyle pad by which the brace, generally, and the joint mechanism, specifically, can be properly positioned relative to the knee of the wearer.

The locations of the pivot points for the pivot plates on the links are set in accordance with parameters which are designed to produce a multiaxis motion of a reference point which will constrain the tibia to slide rearwardly relative to the femur in an initial range of flexion of the knee from a straight leg position and then to rotate relative thereto along an arcuate path. Additionally, the angle between imaginary lines through the pivots of each pivot plate is caused to be greater than a predetermined minimum value which will insure that the joint mechanism has sufficient strength not to break apart in use due to loads which are imposed horizontally across the knee joint.

These and other objects, features and advantages of the present invention will become more apparent from the following description when taken in conjunction with the accompanying drawings which show, for purposes of illustration only, a single preferred embodiment of the present invention.

BRIEF DESCRIPTION OF THE DRAWINGS

FIGS. 7A through 16A are schematic depictions of the outside pivot plate connection between the femoral and tibial links for illustrating the flexion movement thereof at various stages from a fully extended to a fully flexed condition;

FIGS. 7B through 16B are schematic depictions of the inside pivot plate connection between the femoral and tibial links illustrating the flexion movement thereof at various stages from a fully extended to a fully flexed condition;

DETAILED DESCRIPTION OF THE PREFERRED EMBODIMENT

The design of a four bar joint mechanism requires a rational basis or criteria for defining its design parameters since four pivot points are involved and their relative positions are infinitely variable, and whenever these parameters are varied, unless at least three of them remain the same, a different mechanism results. Thus, before discussing the specifics of a knee brace design utilizing a four bar joint mechanism, in accordance with the present invention, a rational design procedure must be arrived at first.

In the case of the present invention, as a result of the experimental analyses which led to the cam mechanism of the above mentioned U.S. Pat. No. 4,890,607 (Townsend design), the which is hereby incorporated by reference, goal is to achieve a four bar joint mechanism which will, similarly, produce an anterior sliding movement of the femur relative to the tibia followed by an essentially unicentric phase as the femur is flexed from its fully extended position. By an "essentially" unicentric phase it is meant that the motion produced by the four bar mechanism during this phase is close enough to being a pivoting movement about a stationary pivot point to be treated as such, bearing in mind the limitations of a four bar mechanism to truly reproduce a single pivot motion and the fact that a limited shifting of the pivot axis of the joint mechanism (to the extent disclosed below) will not have an adverse impact upon the wearer.

Figure 1:
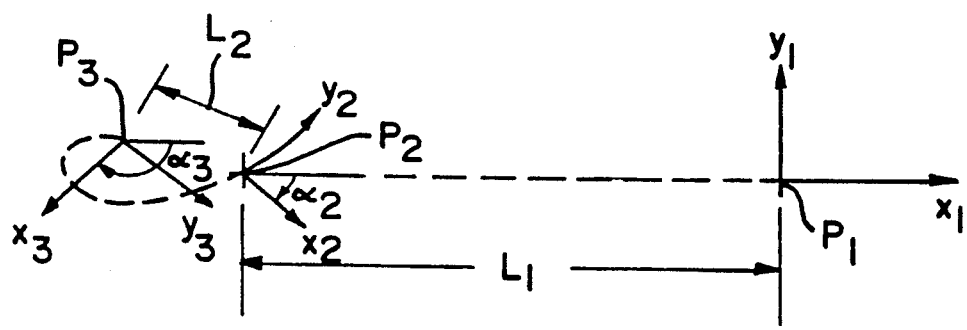
FIGS. 1–4 are schematic depictions for use in explaining design considerations in producing a joint mechanism in accordance with the invention.

To arrive at a four bar joint mechanism which will produce this movement, three positions of the mechanism must be arrived at. This is done, in accordance with the invention, by specifying three positions of the femur relative to the tibia. The three positions are denoted as $P_1$, $P_2$ and $P_3$ in FIG. 1. These positions are defined by the translational motion of a point P (which is a reference point on the femur) and the angle of rotation of the femur from its initial position to the second position ($\alpha_2$) and its angle of rotation from the second position to the third position ($\alpha_3$) As already mentioned, in accordance with the Townsend design, there are two phases of motion which constrain the design of the knee brace mechanism.

PHASE I

The first phase of motion is designed to move point P along a horizontal line from $P_1$ to $P_2$. The distance $L_1$ is a design parameter which can be adjusted to produce different design dimensions and provide a family of braces meeting different translational characteristics. This translation is produced as the femur rotates relative to the tibia through the angle $\alpha_2$. This angle, also, is a design parameter. In the case of the Townsend design, $L_1$ is approximately 8-9 mm and the angle $\alpha_2$ is the first 25° of flexion, and in accordance with this invention, these values are as indicated below.

PHASE II

The second phase of motion moves the reference point P from position $P_2$ to position $P_3$. This motion is specified as another design parameter, the distance $L_2$ that is produced as the femur rotates through an angle $\alpha_{3-\alpha 2}$.

Typical values for these design parameters which have been empirically determined to be suitable are:
$L_1 = 7.5$-$10$ mm
$L_2 = 0.0$ (Points $P_2$ and $P_3$ are identical)
$\alpha_2 = 25°$-$35°$
$\alpha_3 = 120°$-$135°$ As the mechanism moves through its second phase of motion, the objective of the joint mechanism is to keep point P as close to $P_2$ as possible. Therefore, as the femur rotates through $(\alpha_{3-\alpha 2})$, the distance from the reference point P to $P_2$ is to be minimized in order to have an effective knee brace.

FORCE RESISTANCE

Figure 2:
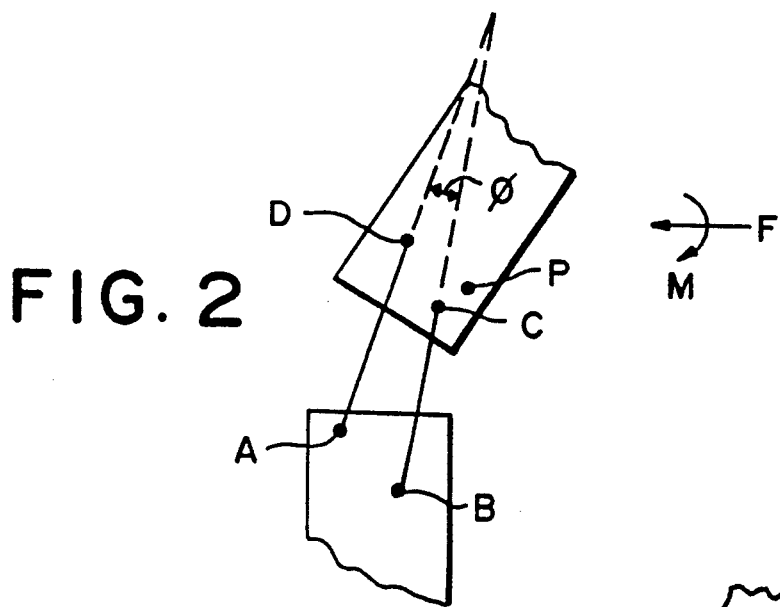

A second design requirement for the joint mechanism, in accordance with the present invention, is that it be able to transmit a horizontal force across the knee joint for all angles of rotation of the femur, without damage to itself, i.e., it will not break up. A typical loading condition is shown in FIG. 2.

In order to transmit the force F across the knee joint, the connecting links AD and BC must not be parallel. If they do become parallel, the mechanism will be unable to resist a horizontal force. For practical purposes, the mechanism will become ineffective if the angle between the two connecting links (denoted as $\Phi$ in the FIG. 2) approaches some minimum value.

The value of the minimum angle $\Phi$ is a design parameter, and minimum values for $\Phi$ in the range of 24°-25° have been proved workable by the present inventors. Reasons for requiring a minimum value of $\Phi$ are that the mechanism, when built, will have some clearance in the joints; and the materials in the mechanism will deflect under stress when the brace is loaded.

DESIGN EQUATIONS

Figure 3:
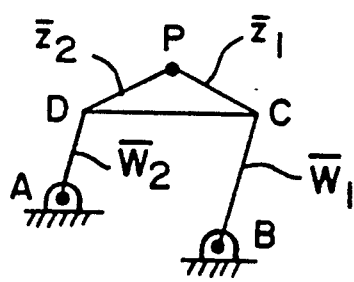

The motion description for the knee brace mechanism defines a three position motion generation problem of the type described, generally, for four bar linkages by Sander & Erdman, (ADVANCED MECHANISM DESIGN: Analysis and Synthesis, by George N. Sandor and Arthur G. Erdman, Prentice-Hall, Inc., Englewood Cliffs, New Jersey 07632, Volume 2, Chapter 2, Pages 92-97 and 122-125). The kinematic synthesis problem is defined and the equations governing the design of 4-bar mechanisms are outlined in this reference, which is hereby incorporated by reference to the extent necessary to complete an understanding of this aspect of the present invention. FIG. 3 shows the general design problem (and corresponds to FIG. 2.57 of Sander & Erdman). Point $P_1$, $P_2$ and $P_3$ are the design locations noted earlier. The angles $\alpha_2$ and $\alpha_3$ are also defined earlier for the present knee brace design.

The design of a 4-bar mechanism is achieved by finding a set of vectors $\overline{W}$ and $\overline{Z}$ which, when combined, form a mechanism as shown in FIG. 3. The equations which control the design (Sandor and Erdman, Page 96) are:

$$W = \frac{\begin{vmatrix} \delta_2 & e^{i\alpha 2} - 1 \\ \delta_3 & e^{i\alpha 3} - 1 \end{vmatrix}}{\begin{vmatrix} e^{i\beta 2} - 1 & e^{i\alpha 2} - 1 \\ e^{i\beta 3} - 1 & e^{i\alpha 3} - 1 \end{vmatrix}}$$

$$Z = \frac{\begin{vmatrix} e^{i\beta 2} - 1 & \delta_2 \\ e^{i\beta 3} - 1 & \delta_3 \end{vmatrix}}{\begin{vmatrix} e^{i\beta 2} - 1 & e^{i\alpha 2} - 1 \\ e^{i\beta 3} - 1 & e^{i\alpha 3} - 1 \end{vmatrix}}$$

where
$\delta_2 = P_2 - P_1$ $\delta_3 = P_3 - P_1$ and $\beta_2$ and $\beta_3$ can be picked arbitrarily. Once two choices of $\beta_2$ and $\beta_3$ are made, these equations define two sides of a four bar mechanism.

Instead of selecting the angles $\beta_2$ and $\beta_3$ arbitrarily, they are determined by selecting locations for the fixed pivot locations A and B. This procedure leads to the following equation for determining $\beta_2$ and as outlined in Sandor and Erdman (page 122-124):

$$D_1 + D_2 e^{i\beta 2} + D_3 e^{i\beta 3} = 0$$

where:
$D_1 = R_3 e^{i\alpha 2} - R_2 e^{i\alpha 3}$ $D_2 = R_1 e^{i\alpha 3} - R^3$ $D_3 = R_2 - R_1 e^{i\alpha 2}$ and for the side $\overline{Z}_2$, $\overline{W}_2$:
$R_1 = P_1 - A$ $R_2 = P_2 - A$ $R_3 = P_3 - A$ while for side $\overline{Z}_1$, $\overline{W}_1$:

$R_1 = P_1 - B$ $R_2 = P_2 - B$ $R_3 = P_3 - B$ $D_1$ is a known vector and, $D_2$ and $D_3$ are vectors of known magnitudes and unknown directions. The directions of the vectors which satisfy the equation lead to the values of $\beta_2$ and $\beta_3$. Knowing $\beta_2$ and $\beta_3$ allows the calculation of W and Z as noted above.

Figure 4:
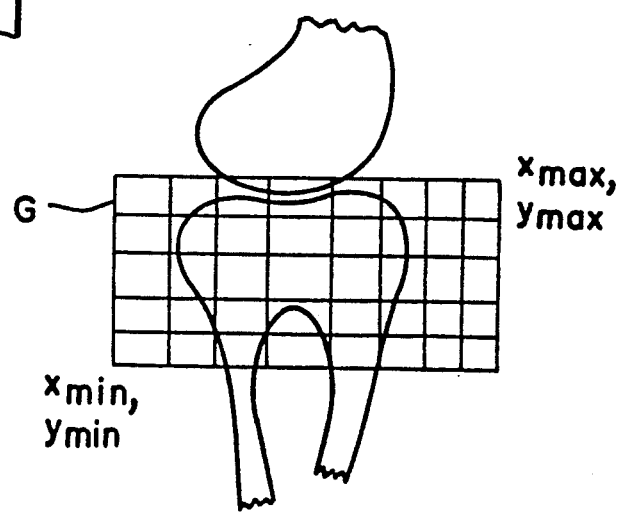

The process just outlined will produce all possible mechanisms which satisfy any prescribed motion using the parameters $P_1$, $L_1$, $L_2$, $\alpha_2$ and $\alpha_3$. The free choices are the locations of the pivot points A and B. To design the joint mechanism for the knee brace in accordance with the present invention, the locations of A and B have been limited to a locating region that allows them to be positioned on the tibia and reference point P has been set at pivot C. This locating region is defined by limits as shown in FIG. 4.

Figure 5:
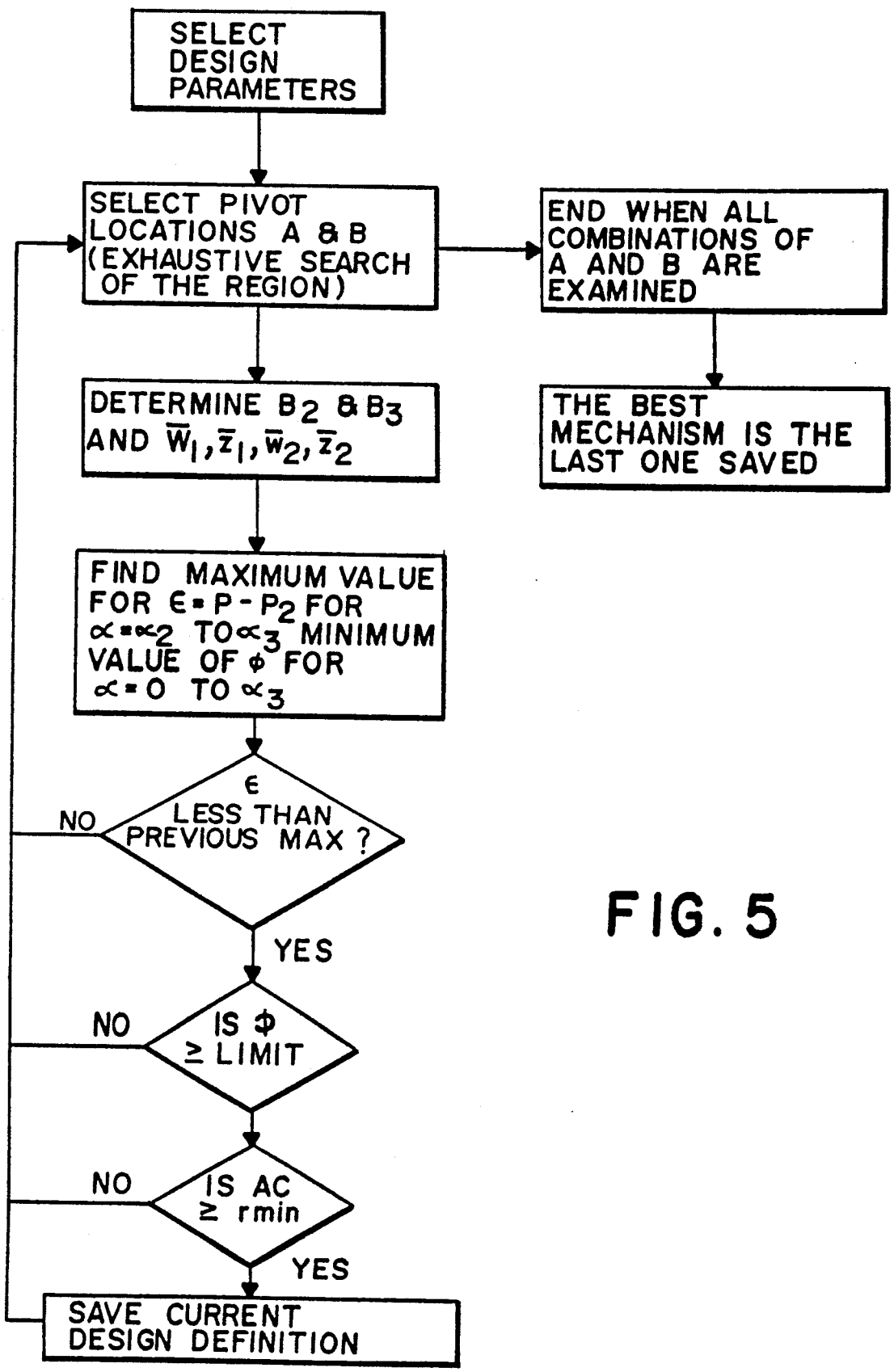
FIG. 5 is a flow diagram depicting an algorithm for use in arriving at the locations for the pivot points of the joint mechanism of the present invention.

The limits are specified as "design parameters" in the flow diagram of FIG. 5, which represents a method by which a suitable design definition can be arrived at, such as by using a computer. This locating region is covered by a grid G and the point at each intersecting pair of grid lines is used as a possible selection of A and B. The spacing of the grid lines in this region is a design parameter and has been set to 1-2 mm by applicants (although not being shown as such in FIG. 4 for simplicity). All combinations of points for the definition of A and B are examined for possible mechanisms for the design of the knee brace.

The criteria used to select the best mechanism from all possible solutions are:

1. The maximum distance point P moves from design location $P_2$ as the femur rotates from $\alpha_2$ to $\alpha_3$ is minimized.

2. The angle between line AD and BC must be greater than a specified minimum valve (typically $\Phi \geq 24.5°$).

In addition, the distance between pivot A and pivot C must be greater than a specified minimum value ($r_{min} = 10$ mm was used). This insures that there is sufficient material around these pivot locations to insure that the brace is strong enough to resist the forces it must carry. This also allows the mechanism to be constructed such that Links AD and BC are on opposite sides of the upper and lower struts (femoral and tibial links) of the brace.

With reference to the above criteria and FIG. 5, the manner in which the best joint mechanisms can be selected, arrived at is clear. First, the design parameters are selected i.e., the grid is defined in terms of $x_{min}$, $y_{min}$, $x_{max}$, $y_{max}$ (based upon the size of the tibia of a leg the brace is to fit) and the grid interval (e.g., 1 mm). Then, sequentially each of the various possible pairs of grid intersection points in the region are considered as locations for pivot points A and B. Then, using the above equations, corresponding values of $\beta_2$ and $\beta_3$ and $W_1$, $Z_1$ and $W_2$, $Z_2$ are determined. Also, since it is desired to keep point P as close to $P_2$ as possible as the femur rotates through the angle between $\alpha_2$ and $\alpha_3$ during the second phase motion, in the next step, the maximum value $\epsilon$ of the difference between P and $P_2$ is determined, and for use in a subsequent step, the minimum value of $\Phi$ is determined. After determining these values, the value of $\epsilon$ just found is subtracted from the prior value of $\epsilon$ and if the result is negative, this first test is failed and a new set of points is examined by returning to the second step (for the first set of points this test will always fail). If this test is passed by the latest value of $\epsilon$ being found to be less than the previous one, a second test is performed to determine if the joint would maintain an angle $\Phi$ above the prescribed minimum (24°-25°), and if not, again, a new set of points is examined by returning to the second step. On the other hand, if the prescribed minimum angle is maintained, the process continues on to a third test which determines whether the distance between pivot A and pivot C is greater than the specified minimum value (e.g., $r_{min} = 10$ mm). If this last test is passed, the design configuration defined by the current set of parameters is saved, and the process restarted at the second step until the last of the possible locations for A and B have been tested, while if not, it is simply restarted.

Once all of the possible combinations of A and B have been exhausted, the last set of parameters saved represents the design configuration for producing the best joint mechanism. As can be appreciated, the criticality does not lie in the particular sequence of steps since, for example, the order of the tests could be change without changing the result. Likewise, while the Sandor & Erdman approach and equations have been utilized, the analysis and synthesis of the mechanism design can be performed utilizing any other known approach and equations pertaining to four bar linkages. What is of primary importance is the manner in which such is applied to solution of the particular problems associated with the present utilization of a four bar linkage to obtain a knee brace which will satisfactorily perform in accordance with the Townsend Design criteria and will meet the requirements determined to be necessary by the present applicants as set forth above.

KNEE BRACE

With the above in mind, a preferred embodiment of a knee brace meeting all of the objects and requirements of the present invention will now be described with reference to FIGS. 6-17.

Figure 6:
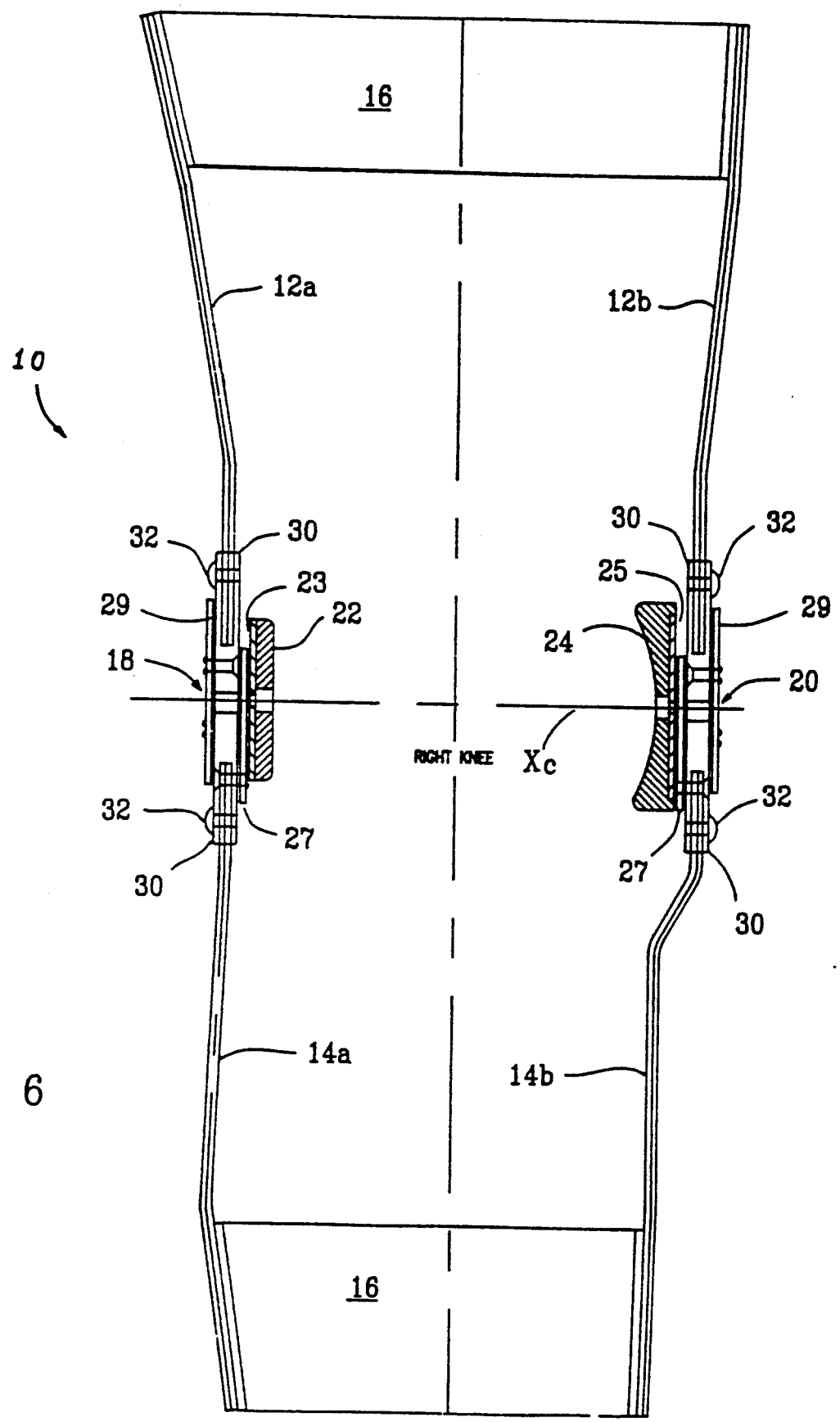
FIG. 6 is a vertical transverse cross section of a knee brace in accordance with a preferred embodiment of the present invention.
Figure 7A:
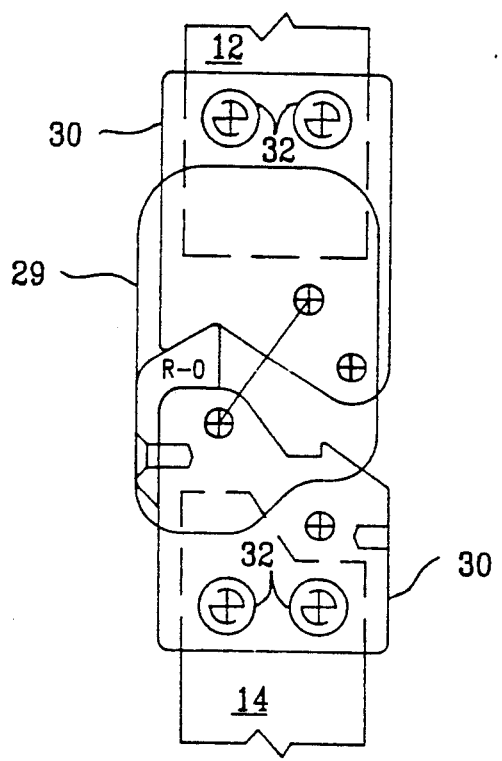
Figure 7B:
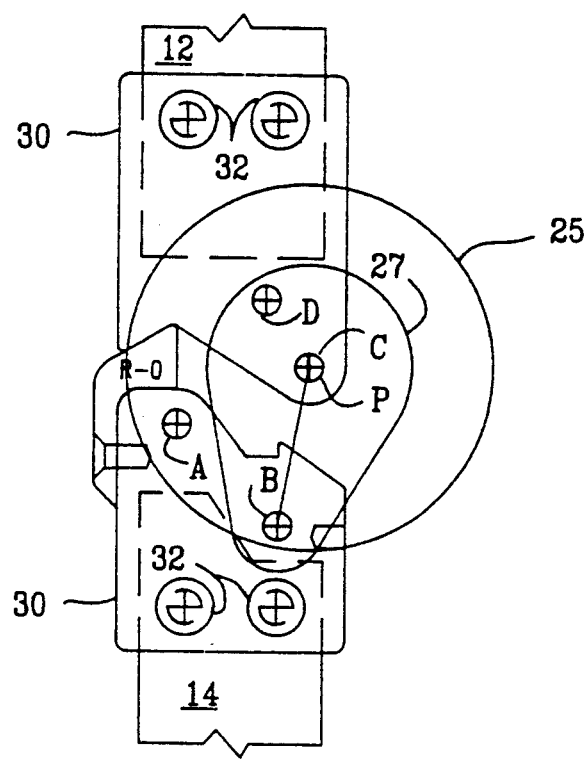
Figure 8A:
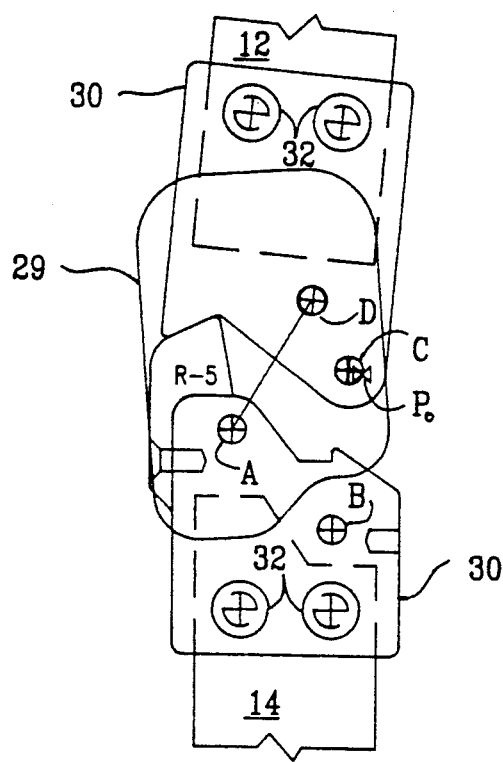
Figure 8B:
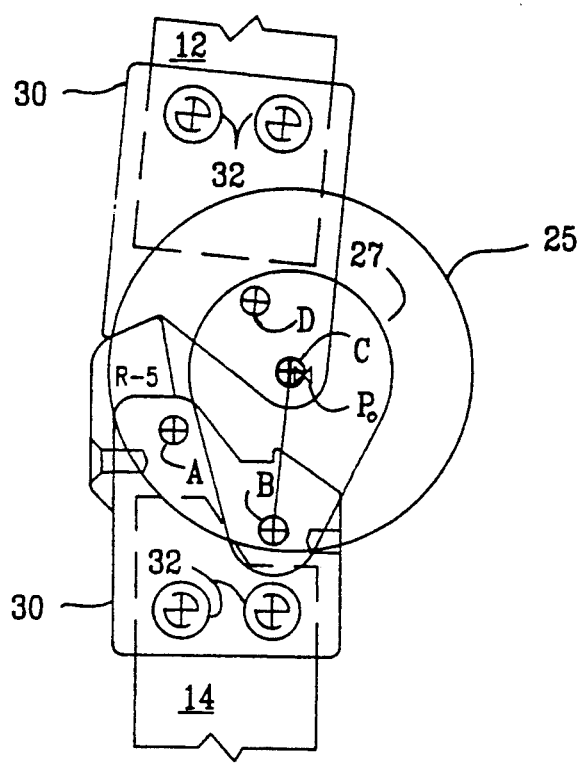
Figure 9A:
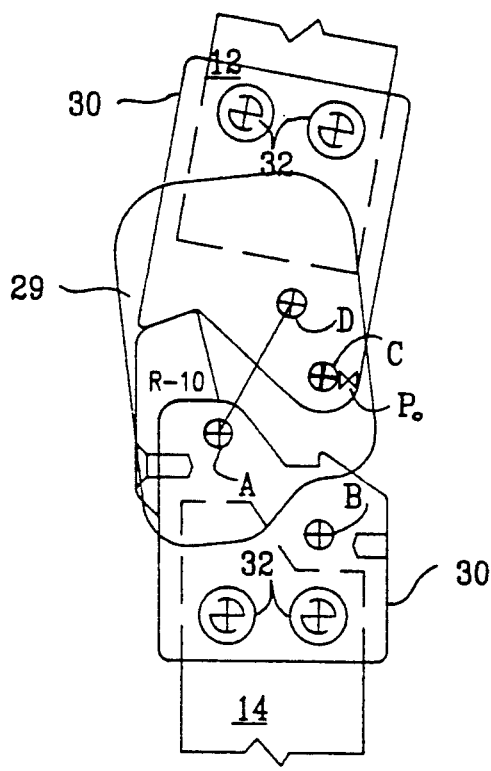
Figure 9B:
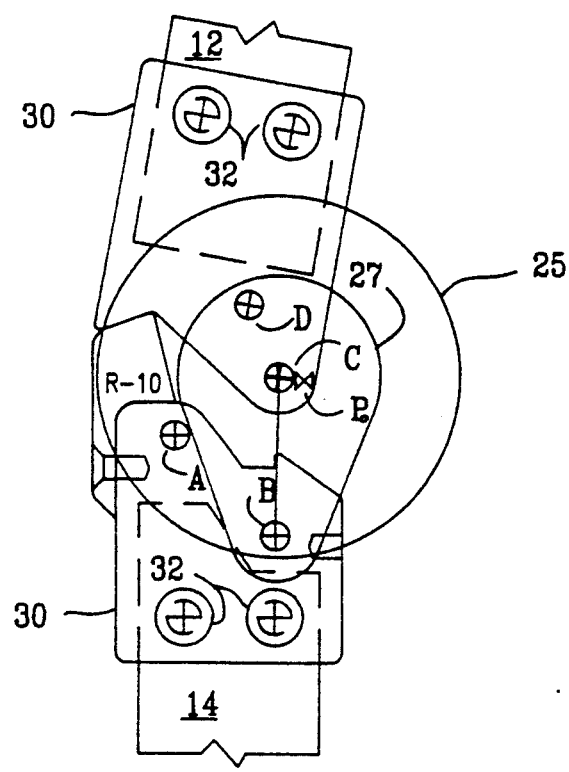
Figure 10A:
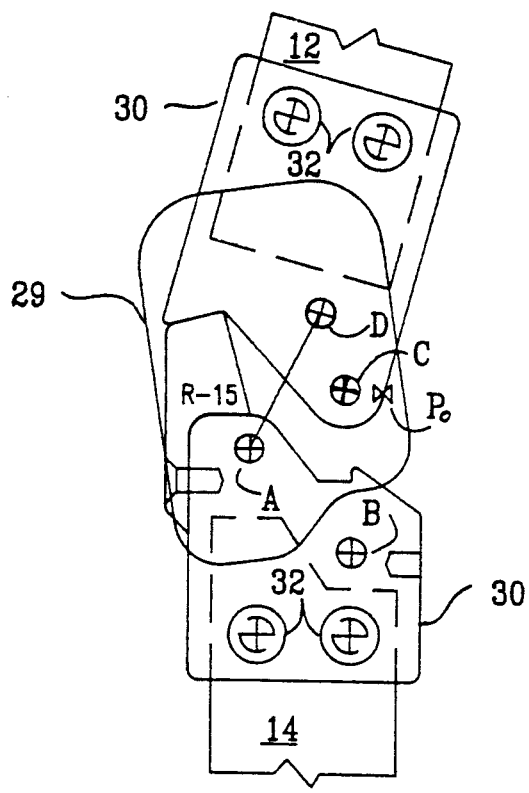
Figure 10B:
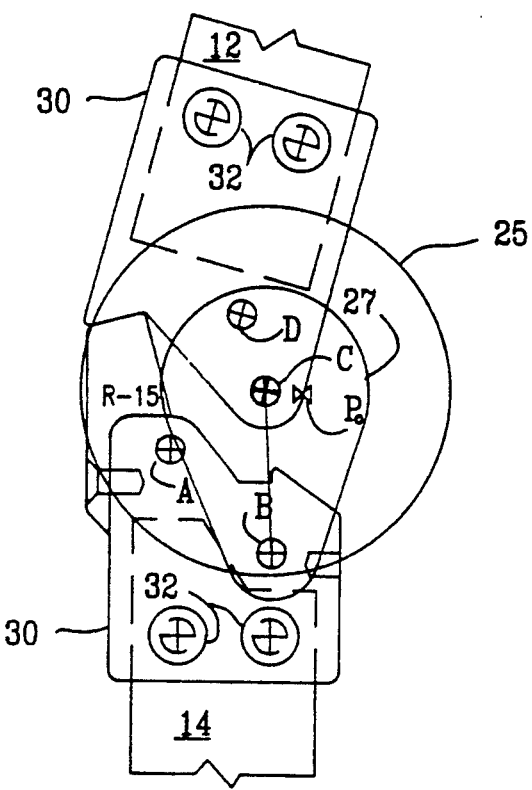
Figure 12A:
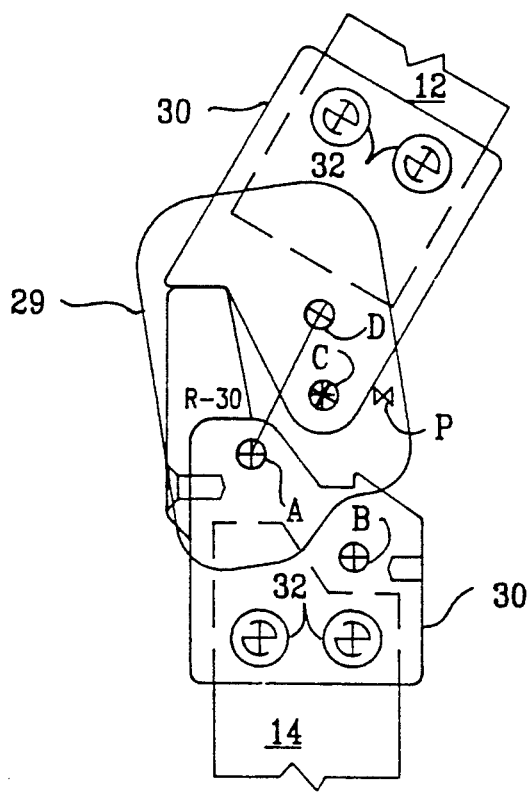
Figure 12B:
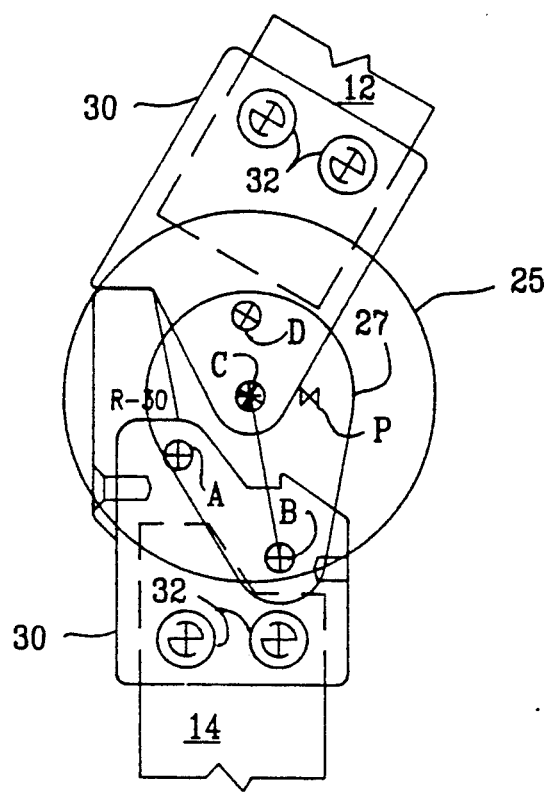
Figure 13A:
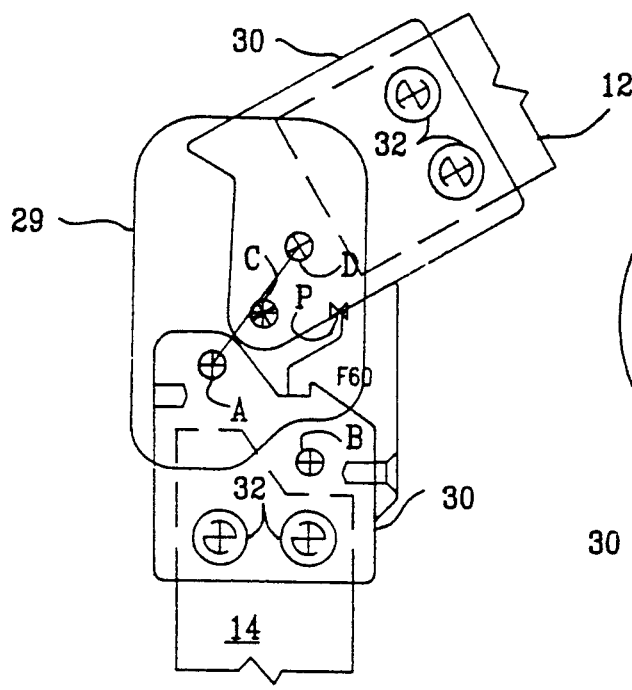
Figure 13B:
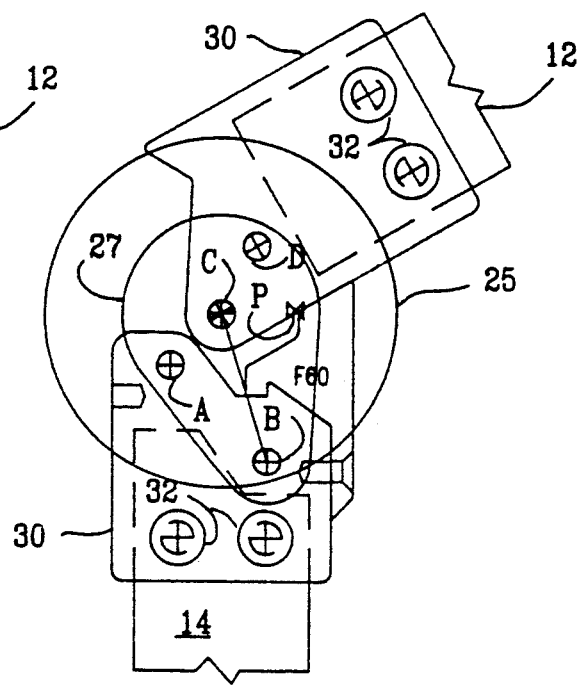
Figure 15A:
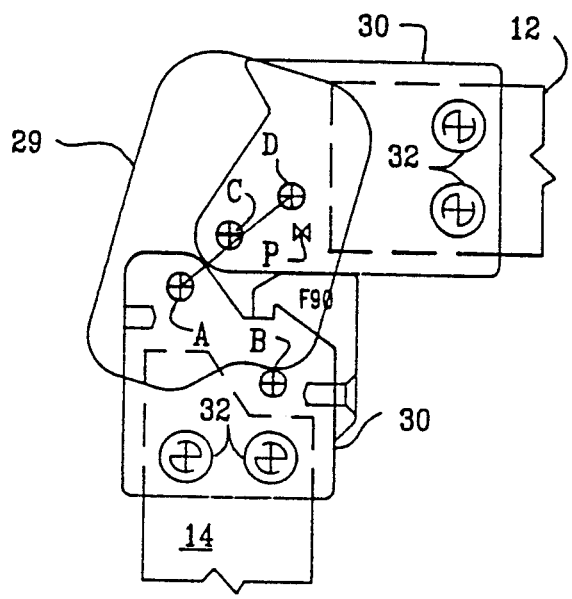
Figure 15B:
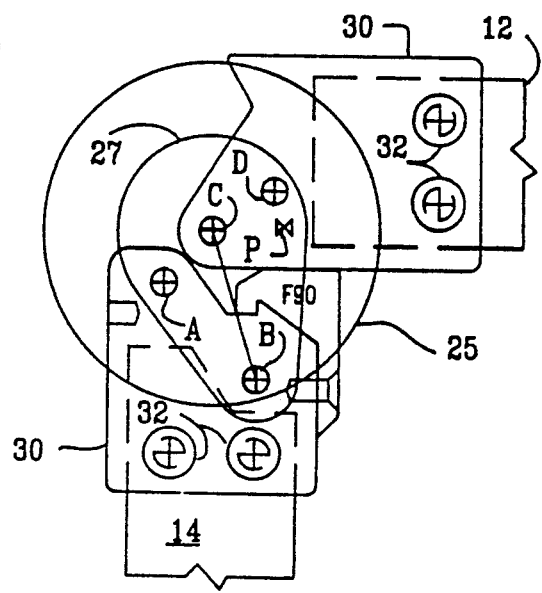

In FIG. 6, it can be seen that the knee brace 10 comprises a pair of femoral links 12a, 12b and a pair of tibial links 14a, 14b which are in the form of a pair of upper struts and a pair of lower struts which can be formed of aluminum, titanium, or fiber and resin composites. A cuff and/or one or more straps 16, of known design, are provided for holding the knee brace on the leg of a person requiring knee support (in the figure, a brace for the right knee is shown and the left would be mirror-imaged relative thereto).

The lateral (outer) side femoral link, 12a is hinged to the lateral side tibial link 14a via a four bar joint mechanism 18 and the medial (outer) side femoral link 14b is hinged to the medial side tibial link 12b via a four bar joint mechanism 20. The medial side joint mechanism 20 differs from the lateral side joint mechanism 18 only with respect to the pads provided on their inner sides for protecting the wearer's leg. The lateral side pad 22 is essentially flat on both sides, while the medial side pad 24 is larger and has a spherically-cupped shape on its side that faces the knee.

This spherically-cupped shape, while not essential, is advantageous in that it allows a quick and easy positioning of the knee brace 10, especially the joint mechanism 18, 20 thereof, on the knee. In particular, by partially flexing the knee (for example, approximately 25 to 35 degrees), the femoral condyle can be felt as a knob at the medial side of the knee and pad 24 can be placed on the femoral condyle as a way of properly locating the joints mechanism so that they will be centered relative to the horizontal axis $x_c$ passing through the femoral condyle. In this way, by attaching the pads 22, 24 to support plates 23, 25, respectively, which are swivelly connected to inner side pivot plates 27 by, e.g., a rivet, they can remain essentially stationary relative to the knee, as it is flexed and extended, thereby avoiding any discomfort to the wearer due to a rubbing of the joint mechanism against the side of the knee. However, it should be appreciated that it is not critical that an exact placement centered on axis $x_c$ be obtained.

Since the remaining details all apply equally to both of the joint mechanisms 18, 20, and to facilitate a side-by-side comparison of the movements at the inner and outer sides of the joint mechanisms 18, 20, they are shown as viewed from a common direction, i.e., as if the joint mechanism was transparent and equivalent to comparing the outer side of the lateral side joint mechanism 18 relative to the inner side of the medial side joint mechanism 20 and vice versa. Because of this approach, the "a" and "b" designations have been dropped from numerals 12 and 14 in FIGS. 7-17.

Outer pivot plates 29 are each pivotally connected to a respective femoral link 12 and a respective tibial link 14, by a pivot pin that is formed, for example, by a rivet, so as to create first and second pivot points A, D. Each inner pivot plate 27 is similarly connected to create third and fourth pivot points B, C.

While each of these pivot pins can be directly connected to a link 12, 14, preferably, these connections are made with a plastic end cap 30 that is fastened on the end of each link 12, 14 by fasteners 32, which may also be rivets. This form of attachment is advantageous in that it allows the joint mechanisms to be assembled and tested separately, and allows the assembled joint mechanisms to be inventoried and subsequently attached to any of variously shaped link struts, such as for legs having small, medium or wide thighs and/or calfs. Furthermore, such a form of attachment is especially advantageous when the link struts are formed of fiber and resin composite materials since the cap 30 enclosing the end of a link 12, 14 formed of such a material will compensate for the low notch strength of the composite material.

In the preferred and illustrated embodiment, the inner link plate 27 generally resembles the shape of an ice cream cone and the outer link plate 29 resembles a rectangle having rounded corners, one of which has been removed. However, such shapes are not essential and can be varied so long as sufficient strength is retained and operation of the joint is not otherwise adversely affected. Furthermore, with other pivot point placements, other shapes may be desirable or even necessary. As should be apparent while called a four "bar" joint mechanism, such a mechanism does not literally require any of the links of which it is comprised to be bar-shaped; by a four bar mechanism, it merely is meant that the joint behaves in a manner which can be schematically represented by four linked bars.

Figure 16A:
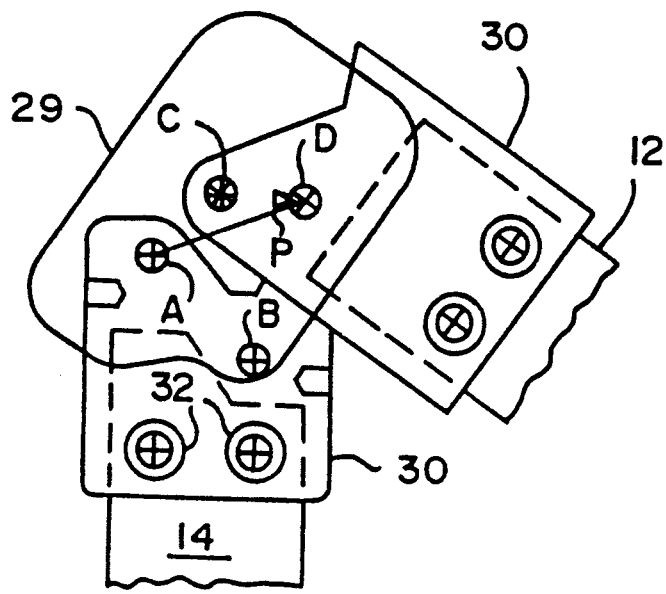
Figure 16B:
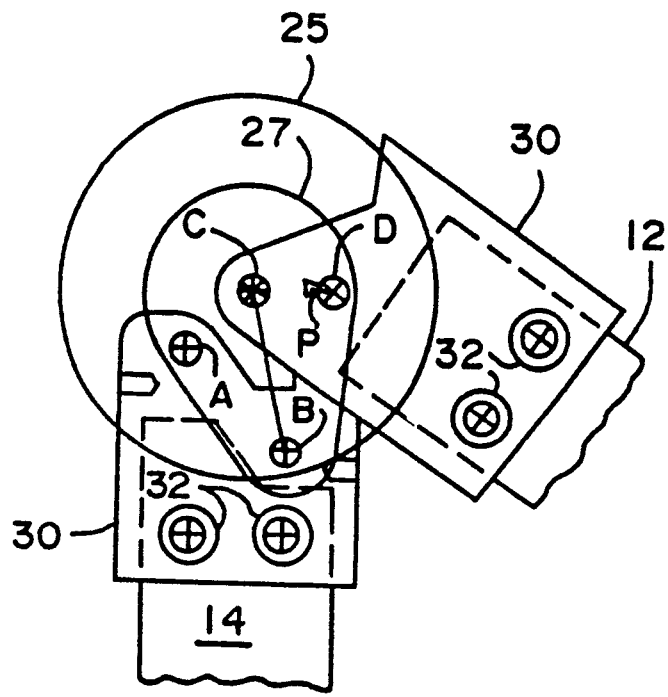

Similarly, the configurations given to the end caps 30 have been chosen, on the one hand, to provide adequate material to securely hold the pivot pins and enable the intended movements of the joint to be obtained while preventing the end cap on femoral link 12 from contacting the end cap on the tibial link 14, and on the other hand, to attach and coact with a set of extension stops R-0 through R-30 (FIGS. 7a, 7b to 12a, 12b) and a set of flexion stops F-60 through F-90 (FIGS. 13a, 13b to 15a, 15b), as well as to inherently create a final flexion stop (FIGS. 16a, 16b). These stops serve to enable it to be possible to impose restrictions on the permissible flexion and/or extension of the knee joint to insure that a user cannot injure himself or herself by either extending or flexing beyond a desirable limit for that person due to injury or deformity. However, the end caps 30 can be reconfigured to work with differently shaped motion stops and/or linkage modifications.

Turning, now, to the operation of this joint mechanism, point P of the above calculations, as noted, has been chosen to correspond to pivot point C. Furthermore, while it would be desirable to locate pivot point C, initially (i.e., in the 0° position of FIGS. 7a, 7b), on axis $x_c$ of the femoral condyle, such is not essential. It has been found that the mechanism will work without problems with the location of pivot pin C situated up to 0.01 to 0.02 mm to the right and up to 3 mm to 5 mm up from axis $x_c$ (as viewed in FIG. 7b), and thereby permitting adaptations to meet physical constraints of any particular knee brace.

The relative positions of the pivot links A-D and B-C, as the joint mechanism is flexed, can be seen in FIGS. 7-15 and show that the angle Φ between them is always greater than 24°-25° throughout the full range of flexion. Furthermore, the initial location of point P, i.e., $P_o$ is shown, in addition, in order to allow the movement of point P, with pivot point C, to be seen.

Figure 17:
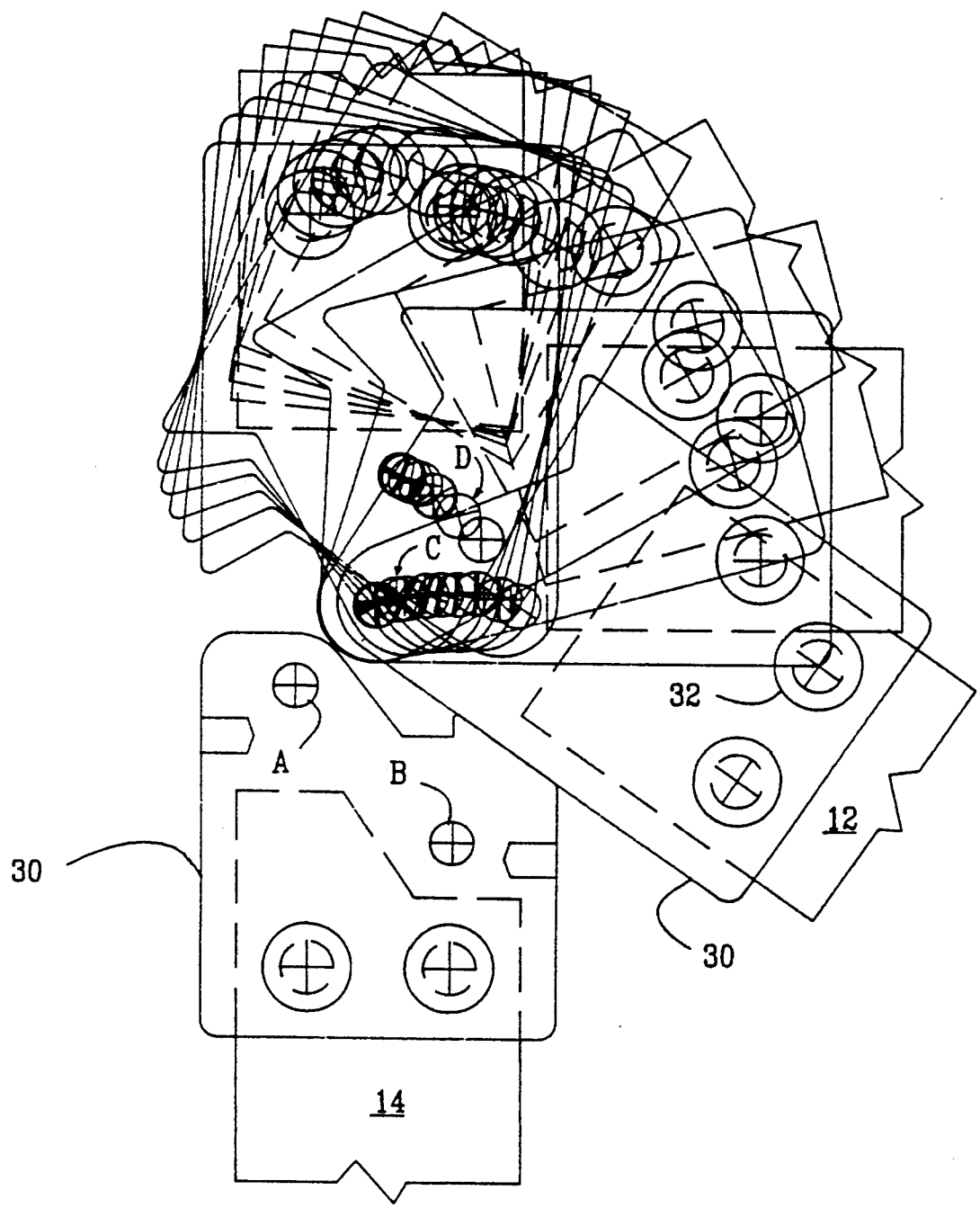
FIG. 17 is a schematic view superposing the views of FIGS. 7A, 7B through 16A, 16B, with the pivot plates removed for clarity, depicting the motion of the femoral pivot points as the femoral link is swung throughout the illustrated range of flexion motion.

Furthermore, from the superposed view of FIG. 17, it can be seen that pivot pin C executes an essentially linear movement corresponding to the anterior movement of the pivot cam pin within the linear cam slot produced by the joint mechanism disclosed in the above-cited Townsend design. In actuality, analysis of the movement shows that a slight up-and-down movement occurs of less than 0.5 mm which, for purposes of the invention and actual usage, is insignificant, so that the motion can be considered, nonetheless, an essentially linear movement. At the same time, it can be seen that pivot pin D, initially remains essentially in a fixed location and then swings downwardly in an essentially unicentric arcuate motion that corresponds to that of the pivot cam which move in the large arcuate slot in the joint mechanism of the Townsend design. Although, it should be recognized, as pointed out above, the motion is not exactly unicentric; for example, despite the fact that pivot point C is in the same location at the beginning and end of the phase 2 motion, it may shift up to about 2 mm, away and then back to this location, in the interim. Of course, it should be recognized that the present invention is not limited to producing the exact same phases of movement as in the Townsend patent, as will be apparent from the permissible range of the values $L_1$, $a_2$ and $a_3$ set forth above. Furthermore, the joint mechanism can be designed to produce more than two phases, or phase 2 could, itself, be subdivided into two or more separate subphases.

Likewise, even though only a single embodiment has been shown and described in accordance with the present invention, it is susceptible to numerous changes and modifications as will be apparent to those skilled in the art. Therefore, the present invention is not limited to the details shown and described herein and instead, encompasses the full scope of the appended claims.

We claim:

1. In a knee brace for controlling movement of the femur relative to the tibia during extension and flexion of a wearer's leg, having a pair of femoral links and a pair of tibial links, one of said femoral links being hinged to one of said tibial links by a joint mechanism at a medial side of the brace and the other of said femoral links being hinged to the other of said tibial links by a joint mechanism at a lateral side of the brace; wherein each said joint mechanism is a four bar linkage having a first pivot plate pivotally connected at a first pivot point to a respective one of said tibial links and at a second pivot point to a respective one of said femoral links, and a second pivot point, pivotally connected at a third pivot point to a respective one of said tibial links and at a fourth pivot point to a respective one of said femoral links, and wherein the relative positions of said pivot points are adapted to produce a motion of a reference point on the femoral condyle, which is an essentially linear, horizontal translation, with reference to an orientation of the brace in which the tibial and femoral links are vertically oriented in a straight leg position, that results in the tibia being constrained to slide posteriorly relative to the femur in a first phase of flexion from said straight leg position, and which is an essentially unicentric arcuate movement about said reference point in a second phase of flexion; and wherein an angle of intersection defined between a portion of an imaginary line drawn through said first and second pivot points and a portion of an imaginary line drawn through said third and fourth pivot points, said portion extending from said said first and third pivot points to a point of intersection of said imaginary lines is at least 24° throughout the full range of flexion from said straight leg position to a fully flexed position.

2. Knee brace according to claim 1, wherein the horizontal translation of said reference position during said first phase is 7.5 mm to 10 mm, and said reference point remains within 2 mm of its position at the end of said first phase during said second phase.

3. Knee brace according to claim 2, wherein said first phase extends from 0° of flexion to 25° to 35+ of flexion, and said second phase extends from the end of the first phase to 120° to 135° degrees of flexion.

4. Knee brace according to claim 1, wherein said first phase extends from 0° of flexion to 25° to 35° of flexion, and said second phase extends from the end of the first phase to 120° to 135° degrees of flexion.

5. Knee brace according to claim 4, wherein, one of the pivot plates of each joint mechanism is located on an inner side of the femoral and tibial links, and the other of said pivot plates is an outer side of the femoral and tibial links.

6. Knee brace according to claim 1, wherein a cushion is swivelly mounted to each of the inner side pivot plates, at the medial side of the knee brace, the cushion is spherically cupped for fitting on the femoral condyle of the wearer.

7. Knee brace according to claim 6, wherein a cushion is swivelly mounted to each of the inner side pivot plates, at the medial side of the knee brace, the cushion is spherically cupped for fitting on the femoral condyle of the wearer.

8. Knee brace according to claim 1, wherein said reference position is on the femoral condyle in proximity to one of said second and fourth pivot points, and wherein the distance from said one of the second and fourth pivot points to the respective one of the first and third pivot points of the same pivot plate is at least 10 mm.

9. Knee brace according to claim 1, wherein each of said femoral and tibial links comprises strut and an end cap secured over an end of the strut; and wherein said pivot points are located on said end caps.

10. Knee brace according to claim 9, wherein the end caps are formed of plastic and said struts are formed of a fiber and resin composite material.

11. In a knee brace for controlling movement of the femur relative to the tibia during extension and flexion of a wearer's leg, having a pair of femoral links and a pair of tibial links, one of said femoral links being hinged to one of said tibial links by a joint mechanism at a medial side of the brace and the other of said femoral links being hinged to the other of said tibial links by a joint mechanism at a lateral side of the brace; wherein each of said femoral and tibial links comprises a strut and an end cap secured over an end of the strut, the end caps being formed of plastic and said struts being formed of a fiber and resin composite material; wherein each said joint mechanism comprises pivot means, interconnecting a portion of the end cap of the tibial link which extends axially beyond an end of the strut over which it is secured and a portion of the end cap of the femoral link which extends axially beyond an end of the strut over which it is secured, for producing a motion of a reference point on the femur which is an essentially linear, horizontal translation that results in the tibia being constrained to slide posteriorly relative to the femur in a first phase of flexion from a straight leg position, and which produces an essentially unicentric arcuate movement about said reference point in a second phase of flexion.

12. Knee brace according to claim 11, wherein the horizontal translation of said reference position during said first phase is 7.5 mm to 10 mm, and said reference point remains within 2 mm of its position at the end of said first phase during said second phase.

13. Knee brace according to claim 12, wherein said first phase extends from 0° of flexion to 25° to 35° of flexion, and said second phase extends from the end of the first phase to 120° to 135° degrees of flexion.

14. Knee brace according to claim 11, wherein said first phase extends from 0° of flexion to 25° to 35+ of flexion, and said second phase extends from the end of the first phase to 120° to 135° degrees of flexion.

15. Knee brace according to claim 11, wherein each said pivot means comprises a four bar linkage having a first pivot plate pivotally connected at a first pivot point to a respective one of said tibial link end caps and at a second pivot point to a respective one of said femoral link end caps, and a second pivot plate, pivotally connected at a third pivot point to a respective one of said tibial link end caps and at a fourth pivot point to a respective one of said femoral link end caps; and wherein an angle of intersection between an imaginary line drawn through said first and second pivot points and an imaginary line drawn through said third and fourth pivot points is at least 24° throughout the full range of flexion from said straight leg position to a fully flexed position.

* * * * *

UNITED STATES PATENT AND TRADEMARK OFFICE
CERTIFICATE OF CORRECTION

PATENT NO. : 5,259,832
DATED : November 9, 1993
INVENTOR(S) : Jeffrey H. Townsend and Robert J. Williams It is certified that error appears in the above-indentified patent and that said Letters Patent is hereby corrected as shown below:

Column 10, line 67, change "point," to --plate--.

Signed and Sealed this

Ninth Day of January, 2001

Attest:

Q. TODD DICKINSON

Attesting Officer     Commissioner of Patents and Trademarks